United States Patent [19]

Moll et al.

[11] Patent Number: 5,500,347
[45] Date of Patent: Mar. 19, 1996

[54] METHOD FOR THE PURIFICATION OF CYTOKERATIN 20 AND ITS USE FOR THE PRODUCTION OF ANTIBODIES

[75] Inventors: Roland Moll; Werner W. Franke, both of Heidelberg, Germany

[73] Assignee: Progen Biotechnik GmbH, Heidelberg, Germany

[21] Appl. No.: 934,656

[22] PCT Filed: Jul. 26, 1991

[86] PCT No.: PCT/EP91/01407

§ 371 Date: Jan. 27, 1993

§ 102(e) Date: Jan. 27, 1993

[87] PCT Pub. No.: WO92/02558

PCT Pub. Date: Feb. 20, 1992

[30] Foreign Application Priority Data

Jul. 27, 1990 [DE] Germany ............... 40 23 945.1

[51] Int. Cl.$^6$ .................. G01N 33/53; G01N 33/574
[52] U.S. Cl. .................. 435/7.23; 436/64; 436/813; 436/547; 436/548; 435/7.21; 530/387.9; 530/388.2; 530/388.8; 530/388.85; 530/389.7; 530/357; 530/412; 530/417
[58] Field of Search .................. 435/7.23, 7.21; 436/64, 813, 547, 548; 530/387.9, 388.2, 388.8, 388.85, 389.7, 357, 412, 417

[56] References Cited

PUBLICATIONS

Moll, et al., *J. Cell Biol.*, vol. III, No. 2, pp. 567–580, Aug. 1990.
Moll R., *Acta Histochem. Suppl.*, vol. 41, pp. 117–27, 1991.
Moll et al., "The Catalog of Human Cytokeratins: Patterns of Expression in Normal Epithelia, Tumors and Cultured Cells", *Cell*, vol. 31, 11–24, (1982).
Gigi et al., "Detection of a Cytokeratin Determinant Common to Diverse Epithelial Cells by a Broadly Cross–Reaction Monclonal Antibody", *The EMBO Journal*, vol. 1, No. 11, 1429–1437 (1982).
Moll et al., "Cytoskeletal Differences Between Human Neuroendocrine Tumors: A Cytoskeletal Protein of Molecular Weight 46,000 Distinguishes Cutaneous from Pulmonary Neuroendocrine Neoplasms", *Differentiation*, 30:165–175, (1985).
Moll et al., "Ein neues epitheliales zytoplasmatisches Strukturprotein (46 000 Protein) mit eingeschränktem Expressionsspektrum: Potentieller histodiagnostischer Marker zur Unterscheidung metastatischer Adenokarzinome", *Verh. Dtsch. Ges. Path.*, 526 (1987).
Moll et al., "Cytokeratins in Normal and Malignant Transitional Epithelium", *American Journal of Pathology*, vol. 132, No. 1 (1988), 123 (5).
Moll, "Cytoskeletal Markers in the Classification of Carcinomas and Their Metastases", *Current Communications in Molecular Biology*, 139 (1989).

*Primary Examiner*—Toni R. Scheiner
*Attorney, Agent, or Firm*—Nikaido, Marmelstein, Murray & Oram

[57] ABSTRACT

In a process for the purification of cytokeratin 20 (CK 20), a cytoskeletal fraction of cells containing CK 20 is produced, the proteins present therein are separated by gel electrophoresis or/and by chromatography and the CK 20 is isolated from the gel or the chromatographic fraction containing CK 20. In a process according to the present invention for the production of antibodies specific for CK 20, purified CK 20 is used for the immunization and then polyclonal or monoclonal antibodies are produced according to well-known methods. These antibodies are used for the immunologically identification of CK 20, or its α-helical central fragment obtained by proteolytic cleavage on tissue sections, in tissue homogenates and in body fluids.

29 Claims, 1 Drawing Sheet

```
IT-A    EKMFMQNLNDXLASYL          (SEQ ID NO:1)
ck 14   VGSEKVTMQNLNDRLASYLDKV    (SEQ ID NO:2)
ck 16   VGSEKVTMQNLNDRLASYLDKV    (SEQ ID NO:2)
ck 15   SGNEKITMQNLNDRLASYLDKV    (SEQ ID NO:3)
ck 19   AGNEKLTMQNLNDRLASYLDKV    (SEQ ID NO:4)
ck 13   TGNEKITMQNLNDRLASYLEKV    (SEQ ID NO:5)
ck 10   SGNEKVTMQNLNDRLASYLDKV    (SEQ ID NO:6)
ck 18   IQNEKETMQSLNDRLASYLDKV    (SEQ ID NO:7)

IT-B    EVQIKQWYETNAPRAG....RDYSAYYRQIE  (SEQ ID NO:8)
ck 14   EVKIRDWYQRQRP.AEI...KDYSAYFKTIE  (SEQ ID NO:9)
ck 16   EVKIRDWYQRQRP.SEI...KDYSPYFKTIE  (SEQ ID NO:10)
ck 15   EVKIHDWYQKQTP.ASP..ECDYSQYFKTIE  (SEQ ID NO:11)
ck 19   EVKIRDWYQKQGP.GPS...RDYSHYYTTIQ  (SEQ ID NO:12)
ck 13   EVKIRDWHLKQSP.ASP..ERDYSPYYKTIE  (SEQ ID NO:13)
ck 10   EGKIKEWYEKHGN.SHQGEPRDYSKYYKTID  (SEQ ID NO:14)
ck 18   ESKIREHHEKKGP...QV..RDWSHYFKTIE  (SEQ ID NO:15)

IT-C    EVNAAPGLNLGVIMNE          (SEQ ID NO:16)
ck 14   VNVEMDAAPGVDLSRILNEMRD    (SEQ ID NO:17)
ck 16   VNVEMDAAPGVDLSRILNEMRD    (SEQ ID NO:17)
ck 15   VNVEMDAAPGVDLTRILAEMRE    (SEQ ID NO:18)
ck 19   VSVEVDSAPGTDLAKILSDMRS    (SEQ ID NO:19)
ck 13   VNVEMDATPGIDLTRVLAEMRE    (SEQ ID NO:20)
ck 10   VNVEMNAAPGVDLTQLLNNMRS    (SEQ ID NO:21)
ck 18   LTVEVDAPKSQDLSIIMADIRA    (SEQ ID NO:22)

IT-D    EKELQSKLSVKATQL           (SEQ ID NO:23)
ck 14   QNLEIELQSQLSMKAS.LENS     (SEQ ID NO:24)
ck 16   QGLEIELQSQLSMKAS.LENS     (SEQ ID NO:25)
ck 15   QELEIELQSQLSMKAG.LENS     (SEQ ID NO:26)
ck 19   QGLEIELQSQLSMKAA.LEDT     (SEQ ID NO:27)
ck 13   QGLEIELQSQLSMKAG.LENT     (SEQ ID NO:28)
ck 10   QALEIELQSQLALKQS.LEAS     (SEQ ID NO:29)
ck 18   QSLEIRLDRMRNLKAS.LENS     (SEQ ID NO:30)
```

METHOD FOR THE PURIFICATION OF CYTOKERATIN 20 AND ITS USE FOR THE PRODUCTION OF ANTIBODIES

The invention concerns a process for the purification of cytokeratin 20, a standard protein material as well as a process for its production and a process for the production of antibodies directed against CK 20 and the use of an antibody which is specific for CK 20 to detect this protein on tissue sections, in tissue homogenates or in body fluids, as well as the use of a standard protein material to detect autoantibodies against CK 20 in blood or serum.

It has been found that the intermediary filament (IF) proteins of the cytokeratin family are effective markers for analyzing the type and state of differentiation of epithelial cells. The epithelial cytokeratins, comprising a family of at least 19 different polypeptides, are expressed in different combinations depending on the course of the cell differentiation. The synthesis of cytokeratins is usually maintained during malignant transformation and this fact could serve as one of the test criteria for epithelial-derived tumours, including tumours of the bladder tract. There was inter alia a need for a reliable detection method which can be easily carried out for determining the location of the primary tumour of metastastic tissue so that effective action can be taken against this primary tumour. The object of the present invention was therefore to provide a way of differentiating various types of tumour cells and detecting the origin of various metastastic tissues which can be carried out easily and as accurately as possible.

A new cytokeratin has now been identified which only occurs in particular cells and thus can serve as a marker to differentiate certain cells and tissues. It has been named cytokeratin 20.

The invention therefore concerns a process for the purification of cytokeratin 20 in which a cytoskeletal fraction from tissues or cells containing CK 20 is prepared, the proteins present therein are separated by gel electrophoresis or/and by chromatography and CK 20 is isolated from the gel or from the chromatography fraction containing the CK 20.

The protein CK 20 has a molecular weight of ca. 46000, an isoelectric point in 9.5 molar urea of ca. 6.1 and is slightly more acidic than non-phosphorylated variants of CK 8. FIG. 1 shows a partial amino acid sequence of CK 20 (denoted IT in this figure; A-D obtained from fragments of CK 20 after digestion with Staphylococcus V8 protease).

According to the present invention it is possible to obtain cytokeratin 20 in such a pure form that it is for example possible to use it to produce specific antibodies. In one embodiment of the present invention the cytoskeletal fraction is produced from duodenal mucosal villi, especially from human tissue. In another embodiment of the invention the cytoskeletal fraction is isolated from culture cells wherein culture cells are preferred which are derived from colon carcinomas, bladder carcinomas or stomach carcinomas. When carrying out a gel electrophoresis in a preferred embodiment of the present invention a first SDS polyacrylamide gel electrophoresis is carried out in a buffer system with an increased salt concentration, subsequently the band containing CK 20 is cut out and the protein is eluted from it and a second polyacrylamide gel electrophoresis is carried out in a buffer system with a lower salt concentration and the now purified CK 20 is isolated from the corresponding band in the gel.

In a further embodiment of the invention, namely separation by chromatography, an anion-exchange chromatography is firstly carried out and then a reversed phase HPLC chromatography. In this case it is in turn preferred that the anion-exchange chromatography is carried out on DEAE cellulose in the presence of urea and using an eluant with a linear gradient of between 0 and 100 mmol/l guanidinium hydrochloride and to subsequently subject the fractions containing CK 20 to HPLC. In this process the fractions containing 38 to 50 mmol/l guanidinium hydrochloride are preferably subjected to HPLC.

The invention furthermore concerns a standard protein material which consists of a reconstituted cytokeratin complex containing CK 20 and a basic cytokeratin from the group of cytokeratins 1 to 8 or consists of the corresponding α-helical central fragments of these proteins produced by proteolytic cleavage. In this connection it is preferred that the standard protein material consists of a complex containing CK 20 and CK 8 or their α-helical central parts.

Such a standard protein material is a suitable agent for use in immunological tests, for example when employing the displacement technique or for carrying out other competitive immunoassays.

The invention in addition concerns a process for the production of a standard protein material containing CK 20 and a basic cytokeratin in which purified CK 20 and a purified basic cytokeratin from the group of the cytokeratins 1 to 8 are together dissolved in an equimolar ratio in a buffer containing urea and the mixture is firstly dialysed against a buffer containing urea and DTT and then against a buffer without urea. A reconstituted filament material is obtained in this process which forms when urea is removed from the buffer. In a preferred embodiment of the invention the cytokeratin complex which is formed is cleaved proteolytically after the production of the standard protein material. The α-helical central fragments of the reconstituted standard protein material are obtained in this manner. This proteolytic cleavage is preferably carried out with chymotrypsin and in an enzyme to substrate ratio of 6:1000 to 10:1000 and digestion times between 30 and 60 minutes.

It is particularly preferred according to the present invention that CK 8 be used as the basic cytokeratin in the production of the standard protein material. It is also in turn preferred that a purified CK 20 be used which has been purified according to the process according to the present invention. In order to produce a standard protein material in another preferred embodiment of the invention, the proteins are dissolved in a buffer containing 8.5 to 10 mol/l urea and 1.5 to 3 mmol/l DTT and the first dialysis is carried out against a buffer containing 3.5 to 4.5 mol/l urea and 1.5 to 3 mmol/l DTT.

The invention in addition concerns a process for the production of antibodies specific for CK 20 by using purified CK 20 to immunize suitable animals and then produce polyclonal or monoclonal antibodies according to known methods. The basic production of polyclonal antibodies as well as of monoclonal antibodies is known to a person skilled in the art and the production of monoclonal antibodies is for example described by Köhler and Milstein in Nature 256 (1975) 495–497. Guinea-pigs are preferably immunized with the purified CK in order to obtain polyclonal antibodies.

In a preferred embodiment of the present invention, CK 20 purified according to the present invention is used.

In order to actually obtain monospecific antibodies which are directed against CK 20 during the production of polyclonal antibodies, it is in turn preferred according to the present invention that these monospecific antibodies are isolated by subjecting the immunoglobulin fraction to an immunoprecipitation and separating antibodies directed against other cytokeratins or/and to an immunoprecipitation and isolating the antibody specific for CK 20. For this purpose all immunoprecipitations known to a person skilled in the art are suitable and finally an antibody is obtained which only reacts immunologically to CK 20. In a preferred embodiment of the present invention, the immunoprecipitation and isolation of antibodies specific for CK 20 is carried out by incubating the immunoglobulin fraction obtained from the experimental animal with a solid phase to which CK 20 has been coupled. When antibodies directed against other cytokeratins are immunoprecipitated and separated, it is preferable to incubate the immunoglobulin fraction obtained with a solid phase to which the electrophoretically purified cytokeratins 8, 18 and 19 or total protein obtained from these cells has been coupled. According to the present invention the immunoprecipitation steps are preferably carried out several times so that all antibodies which are not directed against CK 20 are actually separated from the monospecific antibodies. In turn it is preferred according to the present invention that nitrocellulose strips be used as the solid phase.

The invention furthermore concerns the use of an antibody which is directed against CK 20 for the immunological identification of CK 20 or its α-helical central fragment obtained by proteolytic cleavage on tissue sections, in tissue homogenates and in body fluids. In this connection it is in turn preferred that a homogenate is made from a tissue sample, the intermediary filament proteins present in the homogenate are proteolytically cleaved and the α-helical central fragments released from this into the soluble phase are isolated and quantitatively determined and identified with the aid of the antibody.

A further preferred embodiment of the present invention allows the soluble intermediary filament protein fragments present in body fluids such as blood, blood serum and urine to be immunologically identified and quantitatively determined using the antibody.

The use of the antibody against CK 20 according to the present invention allows a determination of whether this protein is present in tissues, tissue homogenates or body fluids. The presence of this protein enables cells or tissues to be differentiated with respect to the occurrence of CK 20 in particular tissues. Thus adenocarcinomas of the gastrointestinal tract, of the bladder and of Merkel cells of the skin can for example be distinguished from other adenocarcinomas and it is also possible to determine the cellular origin of metastases; hence the CK 20 protein test enables metastases which may be found at completely unrelated sites in the body to be assigned to a primary tumour of one of the aforementioned regions. This allows the actual source of the tumour to be acted on therapeutically by identifying the primary tumour which is often extremely difficult or is not possible to locate at all by previously known methods and thus allows the chances of survival for the patients to be considerably increased. Such a method for distinguishing adenocarcinomas of the gastrointestinal tract, of the bladder or of Merkel cells from other adenocarcinomas or the test for the cellular origin of metastases by examining the presence of CK 20 in the tissue to be examined using antibodies according to the invention which are specific for CK 20 is therefore a further subject matter of the present invention.

Yet another subject matter is the use of a standard protein material according to the present invention to detect autoantibodies against CK 20 in blood or serum. Autoantibodies against CK 20 are for example formed during chemotherapeutic treatment of tumours and can be rated as a criterion for the progress of treatment. Furthermore, such autoantibodies can also be formed in other diseases, e.g. in Morbus Crohn, by which means it is also possible to use the standard protein material to substantiate or to disprove an indication for a disease.

In addition the standard protein material can, as already mentioned, be used in immunological tests which use the antibody according to the present invention to detect CK 20 when for example carrying out an immunoassay of the displacement type.

Immunoassays which can be carried out with the antibodies or the standard protein material according to the present invention are known to a person skilled in the art and do not need to be described in more detail here. In this connection it is of course obvious that the detection is carried out by means of any type of labelling whatsoever of antibodies or standard protein material whereby in this case it appears to be possible to use all known actual test procedures.

The antibody according to the present invention can also be used to carry out a test for cell lesions when this is in an appropriate format, such as that described for example in EP-A 0 057 043. The antibody according to the present invention can also be used to carry out a process like that described in EP-A 0 057 076 in an analogous manner for cytokeratin 20. In this case the antibody according to the present invention is used as the antibody which definitely reacts immunologically.

It is intended to further elucidate the invention by the following examples in conjunction with the figures.

BRIEF DESCRIPTION OF THE DRAWING

In this connection FIG. 1 shows the partial amino acid sequence of CK 20 fragments which were obtained by digestion with Staphylococcus V8 protease and fractionation by reverse phase HPLC. These sequences are compared to the corresponding sequences of various human type I cytokeratins. Amino acids which are identical are shown in bold print. Dots denote omissions which were made in order to show correlations better.

EXAMPLE 1

Production of a Cytoskeletal Preparation

A cytoskeletal fraction was prepared on a large scale from duodenal mucosal villi. The deep-frozen villous material was thawed, homogenized by means of a Polytron homogenizer (Kinematica, Luzern, Switzerland) and extracted for 20 minutes while stirring on ice with a five-fold volume of buffer A (1.5 mol/l KCl, 0.5% Triton X-100, 5 mmol/l EDTA, 0.4 mmol/l phenylmethylsulfonyl fluoride (PMSF), 10 mmol/l Tris-HCl, pH 7.2. A cytoskeletal pellet was obtained by centrifugation (10 minutes at 13000 g, 4° C.) and washing the sediment twice (resuspending by means of a Dounce homogenizer and centrifuging again) in buffer B (5 mmol/l EDTA, 0.4 mmol/l PMSF, 10 mmol/l Tris-HCl, pH 7.2); this was stored at −80° C. Cytoskeletal fractions were also prepared from other tissues and tumours in an analogous manner; in these cases the tissue was cut up into small pieces using scissors or a scalpel before the Polytron homogenization.

Cytoskeletal fractions from culture cells were obtained by a similar procedure. Cells which grew adherently at the bottom of plastic culture flasks were scraped off using a rubber spatula after decanting the culture medium and rinsing twice with phosphate-buffered saline solution (PBS), extracted in buffer A and subsequently washed with buffer B (see Achtstätter et al., Methods Enzymol. 134 (1986) 355–371).

Culture Cells

The following established cell culture lines derived from human carcinomas were used in the investigations:
1. The bladder carcinoma cell lines RT-112, RT-4, T-24 and EJ (see Moll et al., Am. J. Pathol. 132 (1988) 123–144).
2. Several colonic carcinoma cell lines obtained from the American Type Culture Collection (ATCC) and cultured as stated there: HT-29 (ATCC HTB 38); LoVo (ATCC CCL 229); SW 1116 (ATCC CCL 233); LDL-1 (ATCC CCL 221); COLO 320 DM (ATCC CCL 220).
3. Cells of the human mammacarcinoma cell line MCF-7 were cultured as described by Moll and coworkers (Cell 31 (1982) 11–24). In some experiments culture cells were labelled metabolically with $^{35}$S-methionine (Franke and coworkers, Knapp and Franke, Cell 59 (1989), 67–79. "Spontaneous losses of control of cytokeratin gene expression in transformed, non-epithelial human cells occurring at different levels of regulation").

EXAMPLE 2

Preparation of Pure CK 20

In order to obtain CK 20 proteins, two different methods for isolating proteins were used. On the one hand, preparative gel electrophoresis was used (Achtstätter and coworkers, 1986, see example 1) in which cytoskeletal proteins obtained from duodenal mucosal villi were fractionated in a one-dimensional electrophoresis (SDS-PAGE) and visualized by sodium acetate staining. The elution of the protein from the bands which were cut out was either carried out electrophoretically or by incubation of the finely homogenized gel material in a 0.05% aqueous SDS solution. The eluted protein was concentrated by means of vacuum dialysis and precipitated with acetone. The Laemmli system (Laemmli, U.K., Nature 227 (1970) 680–685) or the buffer system with an increased salt concentration (Achtstaetter and coworkers, 1986 (see above)) was used as the SDS-PAGE system and in some cases both were used successively.

A combination of DEAE-cellulose anion-exchange chromatography and "reverse phase" HPLC chromatography was used as a second method with the same starting material (Achtstaetter and coworkers, 1986, see above). The purity of the protein fractions was tested by means of SDS-PAGE. The chromatographic method requires no SDS denaturation and was therefore the method of choice for in vitro experiments of complex formation and reconstitution.

EXAMPLE 3

Production of Specific Polyclonal Antibodies Against CK 20

CK 20 protein purified by preparative gel electrophoresis was used to immunize mice and guinea-pigs using the immunization model of Franke and coworkers (Franke, Denk, Kalt and Schmid (1981) Biochemical and immunological identification of cytokeratin proteins in hepatocytes of mammalian liver tissues. Exp. Cell Res. 131, 299–318). It was possible to isolate an antiserum which contained high titres of antibodies against CK 20 protein but also antibodies against CK 18. Monospecific antibodies against CK 20 protein could be isolated from this serum (without reactivity to CK 18) by absorbing the serum diluted in PBS containing 1% bovine serum albumin and 0.1% sodium azide (or an immunoglobulin fraction produced from this by ammonium sulfate precipitation) several times on nitrocellulose strips to which electro-transferred cytokeratins 8, 18 and 19 from MCF 7 cells or from MCF 7 cell total protein which had been fractionated by SD-SPAGE were bound. The absorption was carried out in each case by incubating for 30 minutes in a small foil sack which was rotated continuously. Between the absorption steps the nitrocellulose strips were regenerated by incubation in 3 mol/l KSCN in PBS and subsequent washing in PBS. About four to eight absorption steps were carried out in succession. In some experiments a positive affinity purification step was carried out on nitrocellulose strips with CK 20 protein separated by means of SDS-PAGE before this counter-absorption; for this the antibodies bound to these strips were eluted by means of 3 mol/l KSCN in PBS and vacuum dialyzed against PBS (Krohne and coworkers, J. Cell Biol. 94 (1982) 749–754). The specificity of the purified antibody preparations was assured by immunoblot analysis after two-dimensional gel electrophoretic fractionation.

EXAMPLE 4

In Vitro Reconstitution of Heterotypical Cytokeratin Complexes and Intermediary Filaments Chromatographically-purified proteins (CK 8, 18 and 20) obtained from cytoskeletal material of duodenal mucosal villi were dissolved in a 10 mmol/l Tris-HCl buffer (pH 8.0) which contained 2.5 mmol/l DTT and 9.5 mol/l urea and (after centrifuging residual insoluble material at 13000 g) either dialyzed singly or in certain approximately stoichiometric mixtures (CK 8+CK 18; CK 8+CK 20) against the same buffer containing DTT but only 4 mol/l urea. By this means it should be possible to achieve a heterotypical complex formation between type I and type II cytokeratins. Aliquots of the solution adjusted to 4 mol/l urea (after centrifugation) were directly subjected as samples to an electrophoresis under non-dissociating conditions in 4 mol/l urea combined with SDS-PAGE in the second dimension.

For the in vitro reconstitution of intermediary (cytokeratin) filaments, chromatographically-purified CK 8 and CK 20 protein were each dissolved at a concentration of 1 mg/ml (protein determination according to Bradford (Bradford M.M., Anal. Biochem. 72, (1976), 248–254)) (buffer see above) and mixed in an equimolar ratio. This mixture (and also solutions of the individual proteins as a control) was dialysed for one hour on swimming membrane filters (Millipore VS 0.025) against 4 mol/l urea in 10 mmol/l Tris-HCl (pH 7.6) containing 2.5 mmol/l DTT and subsequently dialysed for two hours against 10 mmol Tris-HCl (pH 7.6) containing 2.5 mmol/l DTT but no urea. Subsequently, negative staining and electron microscopic examination were carried out (Quinlan et al., J. Mol. Biol. 178 (1984), 365–388).

EXAMPLE 5

Proteolytic Cleavage Experiments

Native cytoskeletal material from duodenal mucosal villi was subjected to a partial proteolytic (chymotryptic) cleavage (Hatzfeld and coworkers, J. Mol. Biol. 197 (1987) 237–255). Enzyme-substrate ratios of 6.6:1000 or 9:1000 and digestion times between 30 and 60 minutes were used in this case. The cleavage products were analyzed by means of SDS-PAGE with subsequent silver staining or immunoblot analysis or by means of two-dimensional gel electrophoresis combined with a tryptic peptide mapping.

EXAMPLE 6

Immunocytochemistry, Methods Used for the Immunofluorescence

Immunoperoxidase and immunoelectron microscopy of cryostatic tissue sections and culture cells were applied as described (Bader et al., Eur. J. Cell Biol. 47 (1988) 300–319; Franke et al., Proc. Natl. Acad. Sci. USA 75, (1978) 5034–5038; Franke et al., Exp. Cell Res. 116 (1978) 429–445; Franke et al., Eur. J. Cell Biol. 19 (1979) 255–268; Franke et al., Exp. Cell Res. 131 (1981) 299–318; Franke et al., J. Cell Biol. 90 (1981) 116–127; Franke et al., Cell 30 (1982) 103–113; Franke et al., Virchows's Archiv A, Pathol. Anat. 411 (1987) 137–147; Jahn et al., Differentiation 36 (1987) 234–254; Knapp and Franke, Cell 59, (1989) 67–79, Moll et al., Am. J. Pathol. 132 (1988) 123–144).

EXAMPLE 7

Method for the Isolation of a Standard

The methods used are described using cytokeratins as an example; the processing technique can, however, be applied to all IF proteins.

7.1 Purification of intact polypeptides

Human cytokeratins (e.g. 8) were isolated from the human culture cell line MCF-7 essentially as described by Achtstaetter et al., Methods Enzymol. 134:355–371 (1986). The cell layer which was scraped off is homogenized (essentially as described by Achtstaetter et al., supra). Individual cytokeratin polypeptides were purified chromatographically by means of anion-exchange chromatography on DEAF-cellulose (DE 52; Whatman Chemical Separation Inc., Clifton, N.J., U.S.A.) in a 8 mol/l (for cytokeratin 8) or 9.5 mol/l (for cytokeratin 20) urea buffer (8 or 9.5 mol/l urea, 2.5 mmol/l dithioerythritol, 30 mmol/l Tris-HCl (pH 8.0)), essentially as described by Hatzfeld & Franke, J. Cell. Biol. 101 (1985) 1826–1841; Achtstaetter et al., 1986 (see above); Bader et al., EMBO J. 5 (1986) 1865–1875; Quinlan et al., J. Mol. Biol. 192 (1986) 337–349. Briefly described: cytoskeletal material was extracted for 2 hours in 9.5 mol/l urea (5 mmol/l dithioerythritol, 10 mmol/l Tris-HCl (pH 8.0)) and the supernatant extract which was obtained after centrifugation at 100,000×g (g=gravitational constant) was dialysed against a 8 or 9.5 mol/l urea buffer and applied to a DEAE-cellulose column which had been equilibrated with this buffer. Bound protein was eluted with a 0 to 100 mmol/l guanidinium-HCl gradient. The polypeptide composition was monitored by SDS-polyacrylamide gel electrophoresis (PAGE). The combined fractions were subjected to a further purification by a reverse-phase high pressure liquid chromatography using 0.01% (v/v) trifluoroacetic acid (TFA) (Fluka, Buchs, Switzerland) as the aqueous solvent A, 0.07% (v/v) TFA in acetonitrile (chromatographic quality, Merck Darmstadt, GFR) as the organic phase (solvent B) and a reverse phase BioRad RP 304 column (BioRad Laboratories, Richmond, Calif., U.S.A.). The peak fractions were pooled, the acetonitrile was removed by evaporation in a vacuum and the fractions were freeze-dried.

7.2 Reconstitution of purified polypeptides to form protofilaments and IF proteins The purified cytokeratins were dissolved in buffer containing 9.5 mol/l urea. Equimolar amounts of type I and type II cytokeratin were mixed at a final concentration of about 0.5 mg/ml and the protofilaments and cytokeratin filaments were obtained by dialysing the polypeptide solution against buffer of a low ionic strength. (The buffers described by Hatzfeld, M. and Franke, J. Cell Biol. 101: 1826–1841 (1985) were used). The formation of protofilaments and cytokeratin filaments was monitored by electron microscopy using negative sample contrast (cf. Hatzfeld and Franke, supra).

7.3 Preparation of α-helical central fragments of cytokeratin by limited proteolysis The proteolytic degradation was carried out with various proteases. In a typical preparation, chymotrypsin (EC 3.4.21.1 from bovine pancreas (e.g. from the Sigma Company, Munich) is used in an enzyme to substrate ratio (weight/weight) of 6.6:1000 for the cytokeratin 8:18 pair and in a ratio of 9:1000 for the cytokeratin 8:20 pair. The digestion time had to be optimized for each chymotrypsin batch. The proteolytic degradation was monitored by gel electrophoretic analysis of the degradation products and optimized for a maximum proportion of rod-shaped central fragments ($M_r$=38000–40000). The optimum is ca. 20 min at 30° C. After the appropriate degradation period, the enzyme activity was stopped by addition of 5 mM phenylmethylsulfonyl fluoride.

7.4 Purification of α-helical central fragments

The proteolytic central fragments and their single fragments were either separated chromatographically on a Sepharose CL6B (Pharmacia LKB, Freiburg) column or directly by reverse-phase high performance liquid chromatography and namely on a reverse-phase BioRad RP304 column using the solvent system described in the above section 7.1. For further purification, the main fractions were dissolved with solvent A in order to reduce the acetonitrile concentration to ca. 20% (v/v) and then applied directly to a My-Bondapak reverse-phase C18 column (Waters Associates, Milford, Mass.). All main fractions were lyophilized and the samples were examined by means of one- and two-dimensional gel electrophoresis for the presence of α-helical central fragments some of which are divided once into two fragments of the central fragment since the cleavage site is located in a short central section where the helical structure is interrupted, and they were used as reference materials and standard materials for calibrating the detection system and for immunizations.

EXAMPLE 8

Selection and Production of Suitable Antibodies

The following methods were used to examine specific antibodies against intermediary filament proteins developed by us and corresponding commercial antibodies for their immunoreactivity with the α-helical fragments of the central part which were obtained as standard material according to example 7:

8.1. Immunoblot (Western blot; reaction with denatured antigen)

Purified fragment proteins (e.g. cytokeratin 8:18 fragments, cytokeratin 8:20 fragments or vimentin fragments) and cytoskeletal preparations from tissue samples (e.g. lymph nodes or liver) were separated gel electrophoretically (sodium dodecylsulfate polyacrylamide gel electrophoresis) before and after a proteolytic digestive reaction with chymotrypsin (compare example 9), the proteins were transferred electrophoretically onto nitrocellulose and incubated with possible specific antibodies. The immune reaction was detected via labelled protein A or labelled anti-mouse antibodies. Antibodies which showed an immune reaction with the α-helical central fragments ($M_r$ 38000–40000; $M_r$ 20000–22000 in the case of basic keratins) were selected.

8.2 Dot-blot (reaction with native or renatured antigen)

Ca. $2\times10^{-6}$ g purified CK 20 proteins (dissolved in $50\times10^{-6}$ l 50 mmol/l $Na_2HPO_4$ buffer, pH 7.4) and supernatant fractions of homogenized tissue samples after digestion with chymotrypsin are directly bound to nitrocellulose (e.g. in a SRC 96 Minifold I dot-blot apparatus from Schleicher and Schuell, Kassel GFR) and incubated with possible specific antibodies. The further procedure is as described under 1.

8.3 ELISA (reaction with native or renatured antigen)

500 ng ($10^{-9}$ g) purified fragment proteins (dissolved in 100 μl ($10^{-6}$ l) 50 mmol/l $NaHCO_3$ buffer, pH 9.6) and 2 μg ($10^{-6}$ g) (in 100 μl [$10^{-6}$ l]) protein from the supernatant fractions of homogenized tissue samples after digestion with chymotrypsin are incubated per well in a 96-well microtitre plate and bound protein is incubated with the possible specific antibodies. The further procedure is as described under 1.

8.4 Immunofluorescence microscopy. Standard method, described in detail e.g. by Ciocca D. R. and Bjercke R. J. (1986) in Methods Enzymol. 121, 562–579.

Antibodies and antisera which were positive according to the above-mentioned methods are $K_s$ 19.2; $K_s$ 18-9B1; $K_s$ 18-27 IV; $K_s$ 8-17.2; $K_s$ pan 1-8; VIM 3B4; IT guinea-pig antiserum (production of guinea-pig antiserum against cytokeratin 20, see example 3), IT mouse antiserum (production see example 3).

8.5 Production of monoclonal antibodies directed against α-helical central fragments In order to produce specific antibodies only in vitro reconstituted filaments formed from the corresponding purified polypeptides were injected for the immunization. In order to produce monoclonal antibodies, female 6–8 week old BALB/c mice were immunized by injecting them with cytoskeletal preparations or reconstituted filaments with $30–300\times10^{-6}$ g protein per injection. The antigens were suspended in phosphate-buffered saline solution (PBS) and emulsified with Freund's adjuvant (complete) for the first injection. In all the following injections Freund's adjuvant (incomplete) was used. The animals were injected subcutaneously three times at intervals of about three weeks and they received an intraperitoneal booster injection of $30–80\times10^{-6}$ g antigen three days before cell fusion. The spleen cells of immunized mice were fused essentially as described by Koehler and Milstein, Nature 256: 495–497 (1975) with mouse myeloma cells of the line Sp3/OAg14, X63-Ag8.653 and NSO/U (described by Shulmann et al., Nature 276: 269–270 (1978); Kearney et al., J. Immunol. 123: 1548–1550 (1979); Clark and Milstein, Somatic Cell Genetics 7: 657–666 (1981)) in a ratio of 10:1. The hybridoma supernatants were tested on frozen sections of human and bovine tissue by means of immunofluorescence microscopy (essentially as described by Achtstaetter et al., Differentiation 31:206–227 (1986)) or on culture cells which were cultured on specially coated glass slides or coverglasses or tested using the enzyme-linked immunoadsorption technique (ELISA) in which the purified antigens were used to coat microtitre plates. Positive clones were subcloned twice by means of controlled dilution. Ig subclasses were determined according to Ouchterlony and Nilsson, L. A. (1978 in: Handbook of Experimental Immunology; Wei Ed., Vol. 1, chapter 19, Blackwell Scientific Publications, Oxford, pp. 1–19).

8.6 Coupling of detector antibodies to peroxidase.

The monoclonal antibodies denoted detector antibodies and specific guinea-pig antiserum were coupled to peroxidase according to a method described by B. Tijssen (Laboratory techniques in biochemistry and molecular biology, Vol. 15: Practice and theory of enzyme immunoassays, R. H. Burdon and P. H. van Knippenberg, eds., Elsevier Amsterdam, New York, Oxford; p. 238):

5 mg peroxidase is dissolved in 0.5 ml sodium carbonate buffer (100 mmol/l, pH 9.2) and prepared for the coupling by oxidizing the enzyme for 2 hours at room temperature and in complete darkness with 0.5 ml of a 10 mmol/l $NaIO_4$ solution. Afterwards the desired antibody (10 mg dissolved in 2 ml 100 mmol/l sodium carbonate buffer, pH 9.2) is added, 0.5 g dry Sephadex G-25 (Pharmacia Co., Freiburg) is added and it is incubated for a further 3 hours in complete darkness. The conjugate which formed in this process is eluted from the Sephadex material using the sodium carbonate buffer and mixed with 1/20 parts by volume of a 0.5% $NaBH_4$ solution in 0.1 mmol/l NaOH. 30 minutes later 1/10 parts by volume of the same solution is added and incubated for 1 hour at 4° C. The conjugate is vacuum-dialysed against PBS and concentrated to ca. 0.5 ml and subsequently fractionated on a Sephadex-G-200 column (Pharmacia Co.) (1.0×50 cm). The fractions (ca. 0.5 ml volume) are tested for their proportion of enzyme activity and antibodies, and the fractions which have a concomitant high Ig concentration and high enzyme activity are pooled.

EXAMPLE 9

Detection and Determination of Metastases in Lymphatic Tissue 9.1 Solubilization of CK 20 proteins and preferably their α-helical central fragments Firstly the wet weight of the lymph node tissue is determined. The tissue is ground in a three-fold volume—in relation to the wet weight—of a phosphate-buffered saline solution (PBS) (10 mmol/l sodium phosphate pH 7.4, 150 mmol/l sodium chloride) using a knife homogenizer until a pulp-like consistency is achieved (the use of a Polytron homogenizer from the Kinematica Company, Luzern/Switzerland is recommended). The homogenate is incubated with chymotrypsin.

For this purpose chymotrypsin is used which has previously been bound to a matrix (CNBr-activated Sepharose 4B, Pharmacia Co., Freiburg): 1 g CNBr-activated Sepharose 4B is swollen for 15 min in 1 mmol/l HCl (gel volume ca. 3.5 ml/g) and washed with a total of 200 ml 1 mmol/l HCl. The hydrochloric acid solution is aspirated and the matrix material is washed with 5 ml coupling buffer (0.5 mol/l NaCl, 0.1 mol/l $NaHCO_3$, pH 8.0). 10 mg chymotrypsin is dissolved in 5 ml coupling buffer and incubated for 2 hours at room temperature with the matrix material in coupling buffer while agitating continuously. Unsaturated coupling sites which remain are subsequently blocked by addition of 5 ml 0.2 mol/l glycine solution (pH 8.0). Subsequently the gel material is washed with an excess of coupling buffer (ca. 50 ml) and 10 ml acetate buffer (0.5 mol/l NaCl, 0.1 mol/l sodium acetate, pH 4.0). Ca. 60% of the chymotrypsin used is bound under these conditions, i.e. the Sepharose 4B gel contains 1.7 mg/ml coupled chymotrypsin. The gel is diluted two-fold in PBS for better handling (chymotrypsin concentration 0.85 mg/ml).

Chymotrypsin (EC 3.4.21.1 from bovine pancreas, e.g. from the Sigma Co. Munich) is added to the tissue pulp in a ratio of 1:1000 (calculated for the wet weight of the tissue). This is followed by an incubation step at 30° C. (preferably in a thermal block, eventually in a water bath). The digestion reaction is stopped after 30 minutes by placing the homogenate on ice for 5 min. The homogenate is centrifuged for 30 min at $2 \times 10^4$ g and the centrifugation supernatant is immediately removed; the coupled chymotrypsin is located in the sediment.

Under these conditions 80 to 95% by weight of the α-helical central fragment material is released from the CK 20 proteins into the supernatant fraction in a state which is still identifiable and some intact CK 20 proteins are also in a soluble state.

9.2 Detection and determination of the vimentin content

Vimentin in the centrifuged supernatant is determined immunologically by a sandwich ELISA. For this, a first antiserum, GP-8 serves as a capture antibody which is directed against the α-helical central fragment and a second monoclonal antibody VIM-3B4 serves as the detector antibody which is directed against another epitope of the α-helical central fragment which is independent and different from the first epitopes. The capture antibody (GP 8) dissolved in 50 mmol/l NaHCO$_3$ (pH 9.6) is coated on microtitre plates ($150 \times 10^{-6}$ l per well) at a concentration of $10 \times 10^{-6}$ g/ml. A purified vimentin fragment at concentrations of 10 ng/ml to 500 ng/ml (dissolved in buffer: 150 mmol/l NaCl, 10 mmol/l Na$_2$HPO$_4$, pH 7.4, 0.05% Tween 20) is used for the standard curve. In order to measure the vimentin concentration in the centrifuged supernatant, this is diluted 1:100 to 1:500 with the latter buffer. The detector antibody VIM 3B4 labelled with peroxidase is diluted to a concentration of $0.5 \times 10^{-6}$ g/ml with buffer (150 mmol/l NaCl, 10 mmol/l Na$_2$HPO$_4$, pH 7.4, 1% bovine serum albumin, 0.05% Tween 20) and $150 \times 10^{-6}$ l is used per well. The substrate used is o-phenylenediamine or ABTS (2,2'-azino-di[3-ethylbenzthiazoline sulfonate (6)]). The vimentin value obtained in this way serves as a reference value for the quantitative evaluation of the other measurement results.

9.3 Determination of cytokeratins and detemination of cytokeratin contents.

The cytokeratins which are present in the centrifuged supernatant are determined immunologically by a sandwich ELISA. A first monoclonal antibody K$_s$ pan 1-8, the so-called capture antibody, which is directed against a first epitope which is typical for the cytokeratins 1 to 8 is used for this. The capture antibody K$_s$ pan 1-8 dissolved in 50 mmol/l NaHCO$_3$ (pH 9.6) is coated on microtitre plates ($150 \times 10^{-6}$ l per well) at a concentration of $2 \times 10^{-6}$ g/ml. The purified cytokeratin fragments are for example used for the standard curve in the combinations 8:18 and 8:20 at concentrations of 5 ng/ml to 500 ng/ml (dissolved in buffer: 150 mmol/l NaCl, 100 mmol/l Na$_2$HPO$_4$, pH 7.4, 0.05% Tween 20). K$_s$ 18-27 IV and K$_s$ 18-9B1 (for cytokeratin 18 fragments) and IT guinea-pig antiserum (for cytokeratin 20 fragments) are used for example as peroxidase-coupled detector antibodies. In order to measure the cytokeratin concentration in the centrifuged supernatant this is diluted 1:100 with buffer (150 mmol/l NaCl, 10 mmol/l Na$_2$HPO$_4$, pH 7.4, 0.05% Tween 20).

For the standardization, known amounts of the cytokeratin standard obtained according to example 7 are subjected to the sandwich ELISA. The enzyme activity which corresponds to the concentration of each of the standardized cytokeratins is plotted against concentration in order to obtain a standard curve from which the concentration of an unknown amount of each of the cytokeratins can be interpolated.

The extent of carcinoma metastases can be expressed by the ratio of the determined cytokeratin and the measured vimentin in the tissue sample.

EXAMPLE 10

Quantitative Determination of Cytokeratin 8:20 in a Sandwich ELISA on Microtitre Plates 10.1 Coating of microtitre plates $0.2 \times 10^{-6}$ g capture antibody K$_s$ pan 1-8 (dissolved in $100-150 \times 10^{-6}$ l 50 mmol/l sodium carbonate buffer, pH 9.6) is pipetted into each well. The plate is covered and incubated overnight at 4° C.

10.2 Washing and blocking

The excess antibody solution is removed from each well by aspiration. Three times in succession $200 \times 10^{-6}$ l washing buffer (PBS-Tween: 150 mmol/l NaCl, 10 mmol/l sodium phosphate buffer pH 7.4, 0.05% Tween 20) is pipetted into each well and removed by inverting the plate. Residual moisture is removed by gently tapping the plate on several layers of paper tissues.

Each well is filled with $200 \times 10^{-6}$ l blocking buffer (150 mmol/l NaCl, 10 mmol/l sodium phosphate buffer pH 7.4, 0.05% Tween 20, 1% bovine serum albumin, 5% sucrose; for longer storage periods 0.01% thimerosal is also added) and incubated for at least 1 hour at room temperature.

10.3 Incubation with antigen or serum samples

Standard protein of cytokeratin 8:20 obtained according to example 7 at concentrations between 5 ng/ml and 500 ng/ml (depending on the respective detector antibody) is taken up in control serum (Monitrol from Merz & Dade or Kontrollogen L and LU from Behring). The control serum is used at a dilution of 1:10 and 1:100. $100 \times 10^{-6}$ l standard protein solution or serum samples (diluted 1:10 and 1:100) is pipetted per well and incubated for 90 min at room temperature. Afterwards it is washed 4 times with $200 \times 10^{-6}$ l washing buffer (PBS-Tween as described above)

10.4 Incubation with detector antibody

Detector antibody (CK 20 guinea-pig antiserum) coupled to peroxidase is diluted in buffer (150 mmol/l NaCl, 10 mmol/l sodium phosphate buffer, pH 7.4, 1% bovine serum albumin) (the optimal concentration is 0.2–0.5 U/ml), $100 \times 10^{-6}$ l of this is pipetted into each well of the microtitre plate and incubated for 90 min at room temperature. Afterwards it is washed twice with $200 \times 10^{-6}$ l washing buffer (PBS-Tween as described above) and four times with 200 μl distilled water.

10.5 Substrate reaction

For a microtitre plate, 1 substrate tablet (10 mg) o-phenylenediamine (Sigma Co.) and $10 \times 10^{-6}$ l 30% H$_2$O$_2$ is either dissolved in 10 ml 0.1M potassium phosphate buffer (pH 6.0) or in citrate-phosphate buffer (0.0347 mol/l citric acid, 0.0667 mol/l disodium hydrogen phosphate; pH 5.0) (when using citrate-phosphate buffer higher absorbances are obtained). $100 \times 10^{-6}$ l substrate solution (incubated at room temperature) is pipetted into each well. The microtitre plate is covered in order to protect the reaction from light (using aluminium foil or the like) and incubated (15–30 min) until an appropriate colour intensity has developed.

10.6 Stopping of the enzyme reaction

The peroxidase reaction is stopped by addition of $50 \times 10^{-6}$ l 12.5% H$_2$SO$_4$ solution. In quantitative determinations the reaction for standard protein and test serum should be stopped after the same period.

19.7 Evaluation

The microtitre plates are measured at 492 nm in an ELISA photometer.

EXAMPLE 11

10 μg standard protein (cytokeratin 20 and cytokeratin 8 reconstituted to form filaments from a stock solution of 0.5 mg/ml in 4 mol/l urea, 10 mmol/l Tris-HCl, pH 7.6, 2 mmol/l dithioerythritol, 5 mmol/l EDTA), dissolved in 100 μl phosphate-buffered saline solution (PBS; 150 mmol/l NaCl, 10 mmol/l sodium phosphate, pH 7.4) is pipetted into each well of a 96-well microtitre plate (e.g. M 129A, Dynatech, Plochingen) and incubated for 16 h at room temperature (RT). Afterwards the wells are emptied, each is washed once with 200 μl PBS and non-saturated binding sites are blocked by incubating for 1 hour at room temperature with 100 μl 1% BSA solution (bovine serum albumin dissolved in PBS). Subsequently the wells are washed three times with 200 μl washing solution each time (0.05% Tween 20, dissolved in PBS), incubated for 1 hour at room temperature with 100 μl patient serum (diluted 1:500 in PBS), washed three times with 200 μl washing solution each time and incubated for 1 hour at room temperature with a peroxidase-coupled anti-human IgM antiserum (rabbit anti-human Ig, μ chain specific; Dako P 322) for the detection of specific IgM antibodies and with a peroxidase-coupled anti-human IgG antiserum (rabbit anti-human Ig, gamma chain specific; Dako P 214) for the detection of specific IgG antibodies each being diluted 1:1000 in a 0.1% BSA solution (in PBS). After washing three times with 200 μl washing solution in each case and twice with 200 μl distilled water in each case, 100 μl substrate solution (10 mg o-phenylenediamine, 10 μl $H_2O_2$: 30% in 10 ml citrate-phosphate buffer: 0.0347 mol/l citric acid, 0.0667 mol/l disodium hydrogen phosphate; pH 5.0) is pipetted into each well. It is developed for 10–30 min (depending on the colour intensity) in darkness, the enzyme reaction is stopped by addition of 50 μl 12.5% $H_2SO_4$ solution and the converted substrate is measured at a wavelength of 492 nm with the aid of an ELISA photometer. Parallel to this reference sera with a low, medium and high titre of cytokeratin 20 autoantibodies are measured for the standardization.

EXAMPLE 12

Immunohistochemical Localization of CK 20 (Protein IT) in Normal and Tumour Tissue of Humans The examination methods were carried out according to known methods such as those cited for example in example 6.

| | |
|---|---|
| 1. Normal tissue | |
| Epithelial cells: | |
| gastric mucous membrane (foveolae epithelium) | +++ |
| small intestinal mucosa | +++ |
| colonic mucosa | +++ |
| epithelium of the urinary tract | +++ |
| Merkel cells | +++ |
| gallbladder mucosa | + |
| thymic reticulum | + |
| prostate | + |
| liver | − |
| pancreas | − |
| kidney | − |
| epidermis | − |
| perspiratory glands | − |
| sebaceous glands | − |
| mammary gland | − |
| salivary gland | − |
| mucous membrane of the mouth | − |
| oesophageal mucosa | − |
| thyroid gland | − |
| lung | − |
| mesothelium | − |
| uterus | − |
| fallopian tube | − |
| epididymis | − |
| Non-epithelial tissue: all of them negative | |
| 2. Tumours | |
| Carcinomas: | |
| adenocarcinoma of the colon | +++ |
| adenocarcinoma of the stomach | ++ |
| adenocarcinoma of the pancreas | ++ |
| adenocarcinoma of the gallbladder | ++ |
| urothelial carcinoma | +++ |
| Merkel cell carcinoma | +++ |
| adenocarcinoma of the lung | −* |
| mammacarcinoma | − |
| adenocarcinoma of the endometrium | −* |
| adenocarcinoma of the ovary | −** |
| adenocarcinoma of the kidney | − |
| thyroid gland carcinoma | − |
| squamous cell carcinoma of the mouth cavity | −* |
| squamous cell carcinoma of the lung | −* |
| squamous cell carcinoma of the cervix | − |
| small-cell carcinoma of the lung | −* |
| All non-epithelial tumours are negative | |

+ = positive
++ = strongly positive
+++ = very strongly positive
− = negative
−* = negative, single cells are, however, sometimes positive
−** = negative, except mucous ovarian carcinoma (++)

The immunohistochemistry was carried out with specific antibodies against CK 20 (from guinea-pig or mouse) and peroxidase-coupled secondary antibodies (anti-mouse or anti-guinea-pig Ig from the goat) or peroxidase-coupled protein A on cryostat tissue sections.

In principle this method can also be applied to paraffin sections (when using the mouse antibody).

The cell lines ATCC HTB 38, ATCC CCC 229, ATCC CCC 233, ATCC CCC 221 and ATCC CCC 220 set forth in the description are available to anyone in the collection of cell lines of the American Type Culture Collection, Rockville, Md., U.S.A. (ATCC) and are listed in the ATCC catalogue.

---

We claim:

1. A process for the purification of cytokeratin 20, CK 20, comprising the steps of:
producing a cytoskeletal fraction from cells containing CK 20,
separating any proteins present by gel electrophoresis, chromatography or by gel electrophoresis and chromatography, and
isolating CK 20 from the gel or from a chromatographic fraction containing the CK 20.

2. The process according to claim 1, wherein said cytoskeletal fraction is produced from duodenal mucosal villi.

3. The process according to claim 1, wherein said cytoskeletal fraction is produced from culture cells which are derived from carcinomas selected from the group consisting of colon carcinomas, bladder carcinomas and gastric carcinomas.

4. The process according to claim 1, wherein said proteins are separated by
carrying out a first SDS polyacrylamide gel electrophoresis in a buffer system with an increased salt concentration,
cutting out any band containing CK 20,
eluting the CK 20 from said band,
subjecting said CK 20 to a second SDS polyacrylamide gel electrophoresis in a buffer system with low salt concentration, and
isolating purified CK 20 from any corresponding band in the gel.

5. The process according to claim 1, wherein said proteins are separated by chromatographic fractionation comprising the steps of:
carrying out anion exchange chromatography; and
subsequently subjecting any fractions containing CK 20 to HPLC.

6. The process according to claim 5, wherein said anion exchange chromatography is carried out on DEAE-cellulose in the presence of urea using an eluant with a linear gradient of between 0 and 100 mmol/l guanidinium hydrochloride.

7. The process according to claim 6, wherein the fractions containing CK 20 contain 38 to 50 mmol/l guanidinium hydrochloride.

8. A protein material comprising a reconstituted cytokeratin complex containing CK 20 and a basic cytokeratin selected from the group consisting of cytokeratins 1 to 8 or corresponding α-helical central fragments of CK 20 and said basic cytokeratin prepared by proteolytic cleavage.

9. The protein material according to claim 8, wherein said basic cytokeratin is CK 8 or α-helical central fragments of CK 8.

10. A process for the production of a standard protein material which contains CK 20 and a basic cytokeratin, comprising the steps of
dissolving purified CK 20 and a purified basic cytokeratin selected from the group consisting of cytokeratins 1 to 8 in an equimolar ratio in a buffer containing urea to produce a mixture,
dialyzing the mixture against a first buffer containing urea and DTT, and
then dialyzing the mixture against a second buffer without urea.

11. The process according to claim 10, wherein any cytokeratin complex which forms is subsequently cleaved proteolytically.

12. The process according to claim 11, wherein said proteolytic cleavage is carried out with chymotrypsin in an enzyme to substrate ratio of 6:1000 to 10:1000 with a digestion period of between 30 and 60 minutes.

13. The process according to claim 10, wherein said purified basic cytokeratin is CK 8.

14. The process according to claim 10 wherein said CK 20 is purified according to claim 1.

15. The process according to claim 10, wherein said purified CK 20 and purified basic cytokeratin are dissolved in a buffer containing 8.5 to 10 mol/l urea and 1.5 to 3 mmol/l DTT, and said first buffer contains 3.5 to 4.5 mmol/l urea and 1.5 to 3 mmol/l DTT.

16. A process for the production of antibodies specific for CK 20, comprising the steps of:

producing a cytoskeletal fraction from cells containing CK 20, separating any proteins present by gel electrophoresis, chromatography or by gel electrophoresis and chromatography, isolating CK 20 from the gel or from the chromatographic fraction containing the CK 20, then immunizing a suitable animal with said CK 20, and isolating any polyclonal or monoclonal antibodies produced.

17. The process according to claim 16, wherein after the production of polyclonal antibodies, monospecific antibodies are isolated by immunoprecipitation and separation of antibodies directed against other cytokeratins or immunoprecipitation and isolation of the antibodies specific for CK 20.

18. The process according to claim 17, wherein said polyclonal or monoclonal antibodies are incubated with a solid phase to which CK 20 has been coupled.

19. The process according to claim 17, wherein said polyclonal or monoclonal antibodies are incubated with a solid phase to which electrophoretically purified cytokeratins 8, 18 and 19 or protein from cells containing cytokeratins 8, 18 and 19 have been coupled.

20. The process according to claim 17, wherein several immunoprecipitation steps are carried out.

21. The process according to claim 18, wherein said solid phase is nitrocellulose strips.

22. The process according to claim 19, wherein said solid phase is nitrocellulose strips.

23. A process for the immunological identification of CK 20 or its α-helical central fragment obtained by proteolytic cleavage, in a sample selected from the group consisting of tissue sections, tissue homogenates and body fluids, comprising contacting said sample with an antibody specific for CK 20 or its α-helical central fragment, and determining any antibody-antigen complexes formed, wherein said antibody is prepared according to claim 16.

24. The process according to claim 23, further comprising forming a homogenate of said sample, proteolytically cleaving any intermediary filament proteins present in said homogenate to release any α-helical central fragments present into the soluble phase, isolating said α-helical central fragments, and identifying and quantitatively determining said fragments using said antibody.

25. The process according to claim 23, wherein said sample contains soluble intermediary filament protein fragments present in body fluids selected from the group consisting of blood, blood serum and urine.

26. A method for the detection of autoantibodies against CK 20 in blood or serum comprising adding a protein material comprising a reconstituted cytokeratin complex containing CK 20 and a basic cytokeratin selected from the group consisting of cytokeratins 1 to 8 or corresponding α-helical central fragments prepared by proteolytic cleavage of CK 20 and said basic cytokeratin, to a blood or serum sample and detecting any autoantibodies which bind to said cytokeratin complex.

27. A method for distinguishing carcinomas of the gastrointestinal tract, the bladder and Merkel cells from other tumors, or for testing for the cellular origin of metastases, comprising determining the presence of CK 20 in a tissue to be examined with antibodies specific for CK 20.

28. The method according to claim 27, wherein said tumors are other carcinomas.

29. A process for the production of antibodies specific for CK 20, comprising the steps of:

producing a cytoskeletal fraction from cells containing CK 20, separating any proteins present, isolating CK 20, then immunizing a suitable animal with said CK 20, and isolating any polyclonal or monoclonal antibodies produced.

\* \* \* \* \*

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Glu  Lys  Met  Phe  Met  Gln  Asn  Leu  Asn  Asp  Xaa  Leu  Ala  Ser  Tyr  Leu
 1               5                        10                        15
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Val  Gly  Ser  Glu  Lys  Val  Thr  Met  Gln  Asn  Leu  Asn  Asp  Arg  Leu  Ala
 1               5                        10                        15

Ser  Tyr  Leu  Asp  Lys  Val
                20
```

( 2 ) INFORMATION FOR SEQ ID NO:3:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Ser  Gly  Asn  Glu  Lys  Ile  Thr  Met  Gln  Asn  Leu  Asn  Asp  Arg  Leu  Ala
 1               5                        10                        15

Ser  Tyr  Leu  Asp  Lys  Val
                20
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ala  Gly  Asn  Glu  Lys  Leu  Thr  Met  Gln  Asn  Leu  Asn  Asp  Arg  Leu  Ala
 1               5                        10                        15

Ser  Tyr  Leu  Asp  Lys  Val
                20
```

( 2 ) INFORMATION FOR SEQ ID NO:5:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Thr Gly Asn Glu Lys Ile Thr Met Gln Asn Leu Asn Asp Arg Leu Ala
1               5                   10                  15

Ser Tyr Leu Glu Lys Val
            20

( 2 ) INFORMATION FOR SEQ ID NO:6:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Ser Gly Asn Glu Lys Val Thr Met Gln Asn Leu Asn Asp Arg Leu Ala
1               5                   10                  15

Ser Tyr Leu Asp Lys Val
            20

( 2 ) INFORMATION FOR SEQ ID NO:7:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ile Gln Asn Glu Lys Glu Thr Met Gln Ser Leu Asn Asp Arg Leu Ala
1               5                   10                  15

Ser Tyr Leu Asp Lys Val
            20

( 2 ) INFORMATION FOR SEQ ID NO:8:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 17..20
        ( D ) OTHER INFORMATION: /note="Xaa indicates that the
        amino acid has been ommitted so that correlations
        between the sequences can be shown more clearly."

( x i ) SEQUENCE DESCRIPTION: SEQ ID NO:8:

Glu Val Gln Ile Lys Gln Trp Tyr Glu Thr Asn Ala Pro Arg Ala Gly
1               5                   10                  15

Xaa Xaa Xaa Xaa Arg Asp Tyr Ser Ala Tyr Tyr Arg Gln Ile Glu
            20                  25                  30

( 2 ) INFORMATION FOR SEQ ID NO:9:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 14

5,500,347

19

20

-continued ( D ) OTHER INFORMATION: /note="Xaa indicates that the
amino acid has been ommitted so that correlations
between the sequences can be shown more clearly."

( i x ) FEATURE:
( A ) NAME/KEY: Peptide
( B ) LOCATION: 18..20
( D ) OTHER INFORMATION: /note="Xaa indicates that the
amino acid has been ommitted so that correlations
between the sequences can be shown more clearly."

( x i ) SEQUENCE DESCRIPTION: SEQ ID NO:9:

```
Glu  Val  Lys  Ile  Arg  Asp  Trp  Tyr  Gln  Arg  Gln  Arg  Pro  Xaa  Ala  Glu
 1              5                       10                      15
Ile  Xaa  Xaa  Xaa  Lys  Asp  Tyr  Ser  Ala  Tyr  Phe  Lys  Thr  Ile  Glu
           20                      25                      30
```

( 2 ) INFORMATION FOR SEQ ID NO:10:

( i ) SEQUENCE CHARACTERISTICS:
( A ) LENGTH: 31 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 14
( D ) OTHER INFORMATION: /note="Xaa idicates that the
amino acid has been ommitted so that correlations
between the sequences can be shown more clearly."

( i x ) FEATURE:
( A ) NAME/KEY: Peptide
( B ) LOCATION: 18..20
( D ) OTHER INFORMATION: /note="Xaa indicates that the
amino acid has been ommitted so that correlations
between the sequences can be shown more clearly."

( x i ) SEQUENCE DESCRIPTION: SEQ ID NO:10:

```
Glu  Val  Lys  Ile  Arg  Asp  Trp  Tyr  Gln  Arg  Gln  Arg  Pro  Xaa  Ser  Glu
 1              5                       10                      15
Ile  Xaa  Xaa  Xaa  Lys  Asp  Tyr  Ser  Pro  Tyr  Phe  Lys  Thr  Ile  Glu
           20                      25                      30
```

( 2 ) INFORMATION FOR SEQ ID NO:11:

( i ) SEQUENCE CHARACTERISTICS:
( A ) LENGTH: 31 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 14
( D ) OTHER INFORMATION: /note="Xaa indicates that the
amino acid has been ommitted so that correlations
between the sequences can be shown more clearly."

( i x ) FEATURE:
( A ) NAME/KEY: Peptide
( B ) LOCATION: 18..19
( D ) OTHER INFORMATION: /note="Xaa indicates that the
amino acid has been ommitted so that correlations
between the sequences can be shown more clearly."

( x i ) SEQUENCE DESCRIPTION: SEQ ID NO:11:

```
Glu  Val  Lys  Ile  His  Asp  Trp  Tyr  Gln  Lys  Gln  Thr  Pro  Xaa  Ala  Ser
 1              5                       10                      15
```

```
Pro  Xaa  Xaa  Glu  Cys  Asp  Tyr  Ser  Gln  Tyr  Phe  Lys  Thr  Ile  Glu
     20                   25                       30
```

( 2 ) INFORMATION FOR SEQ ID NO:12:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 14
        ( D ) OTHER INFORMATION: /note="Xaa indicates that the
            amino acid has been ommitted so that correlations
            between the sequences can be shown more clearly."

( i x ) FEATURE:
        ( A ) NAME/KEY: Peptide
        ( B ) LOCATION: 18..20
        ( D ) OTHER INFORMATION: /note="Xaa indicates that the
            amino acid has been ommitted so that correlations
            between the sequences can be shown more clearly."

( x i ) SEQUENCE DESCRIPTION: SEQ ID NO:12:

```
Glu  Val  Lys  Ile  Arg  Asp  Trp  Tyr  Gln  Lys  Gln  Gly  Pro  Xaa  Gly  Pro
1                   5                        10                       15

Ser  Xaa  Xaa  Xaa  Arg  Asp  Tyr  Ser  His  Tyr  Tyr  Thr  Thr  Ile  Gln
     20                   25                       30
```

( 2 ) INFORMATION FOR SEQ ID NO:13:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 14
        ( D ) OTHER INFORMATION: /note="Xaa indicates that the
            amino acid has been ommitted so that correlations
            between the sequences can be shown more clearly."

( i x ) FEATURE:
        ( A ) NAME/KEY: Peptide
        ( B ) LOCATION: 18..19
        ( D ) OTHER INFORMATION: /note="Xaa indicates that the
            amino acid has been ommitted so that correlations
            between the sequences can be shown more clearly."

( x i ) SEQUENCE DESCRIPTION: SEQ ID NO:13:

```
Glu  Val  Lys  Ile  Arg  Asp  Trp  His  Leu  Lys  Gln  Ser  Pro  Xaa  Ala  Ser
1                   5                        10                       15

Pro  Xaa  Xaa  Glu  Arg  Asp  Tyr  Ser  Pro  Tyr  Tyr  Lys  Thr  Ile  Glu
     20                   25                       30
```

( 2 ) INFORMATION FOR SEQ ID NO:14:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 14

(D) OTHER INFORMATION: /note="Xaa indicates that the amino acid has been ommitted so that correlations between the sequences can be shown more clearly."

(xi) SEQUENCE DESCRIPTION: SEQ ID NO:14:

Glu Gly Lys Ile Lys Glu Trp Tyr Glu Lys His Gly Asn Xaa Ser His
1               5                   10                  15

Gln Gly Glu Pro Arg Asp Tyr Ser Lys Tyr Tyr Lys Thr Ile Asp
            20              25              30

(2) INFORMATION FOR SEQ ID NO:15:

(i) SEQUENCE CHARACTERISTICS:
    (A) LENGTH: 31 amino acids
    (B) TYPE: amino acid
    (D) TOPOLOGY: linear (ii) MOLECULE TYPE: peptide (ix) FEATURE:
    (A) NAME/KEY: Peptide
    (B) LOCATION: 14..16
    (D) OTHER INFORMATION: /note="Xaa indicates that the amino acid has been ommitted so that correlations between the sequences can be shown more clearly."

(ix) FEATURE:
    (A) NAME/KEY: Peptide
    (B) LOCATION: 19..20
    (D) OTHER INFORMATION: /note="Xaa indicates that the amino acid has been ommitted so that correlations between the sequences can be shown more clearly."

(xi) SEQUENCE DESCRIPTION: SEQ ID NO:15:

Glu Ser Lys Ile Arg Glu His His Glu Lys Lys Gly Pro Xaa Xaa Xaa
1               5                   10                  15

Gln Val Xaa Xaa Arg Asp Trp Ser His Tyr Phe Lys Thr Ile Glu
            20              25              30

(2) INFORMATION FOR SEQ ID NO:16:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:16:

Glu Val Asn Ala Ala Pro Gly Leu Asn Leu Gly Val Ile Met Asn Glu
1               5                   10                  15

(2) INFORMATION FOR SEQ ID NO:17:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (xi) SEQUENCE DESCRIPTION: SEQ ID NO:17:

Val Asn Val Glu Met Asp Ala Ala Pro Gly Val Asp Leu Ser Arg Ile
1               5                   10                  15

Leu Asn Glu Met Arg Asp
            20

(2) INFORMATION FOR SEQ ID NO:18:

( i ) SEQUENCE CHARACTERISTICS:
   ( A ) LENGTH: 22 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:18:

```
Val Asn Val Glu Met Asp Ala Ala Pro Gly Val Asp Leu Thr Arg Ile
1               5                   10                  15
Leu Ala Glu Met Arg Glu
                20
```

( 2 ) INFORMATION FOR SEQ ID NO:19:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:19:

```
Val Ser Val Glu Val Asp Ser Ala Pro Gly Thr Asp Leu Ala Lys Ile
1               5                   10                  15
Leu Ser Asp Met Arg Ser
                20
```

( 2 ) INFORMATION FOR SEQ ID NO:20:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:20:

```
Val Asn Val Glu Met Asp Ala Thr Pro Gly Ile Asp Leu Thr Arg Val
1               5                   10                  15
Leu Ala Glu Met Arg Glu
                20
```

( 2 ) INFORMATION FOR SEQ ID NO:21:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

```
Val Asn Val Glu Met Asn Ala Ala Pro Gly Val Asp Leu Thr Gln Leu
1               5                   10                  15
Leu Asn Asn Met Arg Ser
                20
```

( 2 ) INFORMATION FOR SEQ ID NO:22:

( i ) SEQUENCE CHARACTERISTICS:
      ( A ) LENGTH: 22 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:22:

```
        Leu  Thr  Val  Glu  Val  Asp  Ala  Pro  Lys  Ser  Gln  Asp  Leu  Ser  Ile  Ile
        1                  5                        10                       15

Met  Ala  Asp  Ile  Arg  Ala
                       20
```

( 2 ) INFORMATION FOR SEQ ID NO:23:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
        Glu  Lys  Glu  Leu  Gln  Ser  Lys  Leu  Ser  Val  Lys  Ala  Thr  Gln  Leu
        1                  5                        10                       15
```

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 17
        ( D ) OTHER INFORMATION: /note="Xaa indicates that the
            amino acid has been ommitted so that correlations
            between the sequences can be shown more clearly."

( x i ) SEQUENCE DESCRIPTION: SEQ ID NO:24:

```
        Gln  Asn  Leu  Glu  Ile  Glu  Leu  Gln  Ser  Gln  Leu  Ser  Met  Lys  Ala  Ser
        1                  5                        10                       15

Xaa  Leu  Glu  Asn  Ser
                       20
```

( 2 ) INFORMATION FOR SEQ ID NO:25:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 17
        ( D ) OTHER INFORMATION: /note="Xaa indicates that the
            amino acid has been ommitted so that correlations
            between the sequences can be shown more clearly."

( x i ) SEQUENCE DESCRIPTION: SEQ ID NO:25:

```
        Gln  Gly  Leu  Glu  Ile  Glu  Leu  Gln  Ser  Gln  Leu  Ser  Met  Lys  Ala  Ser
        1                  5                        10                       15

Xaa  Leu  Glu  Asn  Ser
                       20
```

( 2 ) INFORMATION FOR SEQ ID NO:26:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
    ( A ) NAME/KEY: Peptide
    ( B ) LOCATION: 17
    ( D ) OTHER INFORMATION: /note="Xaa indicates that the amino acid has been ommitted so that correlations between the sequences can be shown more clearly."

( x i ) SEQUENCE DESCRIPTION: SEQ ID NO:26:

```
Gln Glu Leu Glu Ile Glu Leu Gln Ser Gln Leu Ser Met Lys Ala Gly
1               5                   10                  15

Xaa Leu Glu Asn Ser
            20
```

( 2 ) INFORMATION FOR SEQ ID NO:27:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 17
    ( D ) OTHER INFORMATION: /note="Xaa indicates that the amino acid has been ommitted so that correlations between the sequences can be shown more clearly."

( x i ) SEQUENCE DESCRIPTION: SEQ ID NO:27:

```
Gln Gly Leu Glu Ile Glu Leu Gln Ser Gln Leu Ser Met Lys Ala Ala
1               5                   10                  15

Xaa Leu Glu Asp Thr
            20
```

( 2 ) INFORMATION FOR SEQ ID NO:28:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 17
    ( D ) OTHER INFORMATION: /note="Xaa indicates that the amino acid has been ommitted so that correlations between the sequences can be shown more clearly."

( x i ) SEQUENCE DESCRIPTION: SEQ ID NO:28:

```
Gln Gly Leu Glu Ile Glu Leu Gln Ser Gln Leu Ser Met Lys Ala Gly
1               5                   10                  15

Xaa Leu Glu Asn Thr
            20
```

( 2 ) INFORMATION FOR SEQ ID NO:29:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 17

(D) OTHER INFORMATION: /note="Xaa indicates that the amino acid has been ommitted so that correlations between the sequences can be shown more clearly."

(xi) SEQUENCE DESCRIPTION: SEQ ID NO:29:

```
Gln Ala Leu Glu Ile Glu Leu Gln Ser Gln Leu Ala Leu Lys Gln Ser
 1               5                  10                  15

Xaa Leu Glu Ala Ser
            20
```

(2) INFORMATION FOR SEQ ID NO:30:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 17
        (D) OTHER INFORMATION: /note="Xaa indicates that the amino acid has been ommitted so that correlations between the sequences can be shown more clearly."

(xi) SEQUENCE DESCRIPTION: SEQ ID NO:30:

```
Gln Ser Leu Glu Ile Arg Leu Asp Arg Met Arg Asn Leu Lys Ala Ser
 1               5                  10                  15

Xaa Leu Glu Asn Ser
            20
```